United States Patent [19]
Kozel

[11] Patent Number: 5,677,137
[45] Date of Patent: Oct. 14, 1997

[54] METHOD TO IDENTIFY IMMUNOCOMPROMISED PATIENTS AT HIGH RISK FOR CRYPTOCOCCOSIS

[75] Inventor: Thomas Randall Kozel, Reno, Nev.

[73] Assignee: Research Development Foundation, Carson City, Nev.

[21] Appl. No.: 236,331

[22] Filed: May 2, 1994

[51] Int. Cl.$^6$ .................................................... G01N 33/53
[52] U.S. Cl. ...................... 435/7.32; 435/7.92; 435/7.95; 436/528; 436/531; 436/532
[58] Field of Search .................................. 435/7.92, 7.93, 435/7.94, 7.95, 911, 975, 7.32; 436/528, 531, 811, 532

[56] References Cited

PUBLICATIONS

Reiss et al, Diagnostic Immunology 2:109–115, 1984.
Abbas et al., Cellular and Molecular Immunology, 1991 by W. B. Saunders Co. Philadelphia pp. 377–397 and 303–305.
Harlow et al. "Antibodies a Laboratory Manual", 1998 by Cold Spring Harbor Laboratory pp. 234–237.
Casadevall et al, Journal of Immunological Methods 154:27–35, 1992.
Kozel et al, Journal of Immunological Methods, 107:53–58, 1988.
Jawetz et al, Review of Medical Microbiology, 1982 by Lange Medical Publications Los Altos CA pp. 299–300.
Brandt et al., Bioch. Biophys acta, 386:196 (1975).
Ternynck et al, Ann. Immunol. 127 C:197 (1976).
Kozel et al, Infection & Immunity, 43(3):879 (1984).
Small et al, Infection & Immunity, 54(3):742 (1986).
Eckert et al., Infection & Immunity, 55(8):1895 (1987).
Cherniak et al, Diag. & Clin Immunol., 5:344 (1988).
Dromer et al, Infection & Immunity, 55(3):742 (1987).
Dromer et al, Scand. J. Infec. Dis., 20:283 (1988).

Primary Examiner—Paula K. Hutzell
Assistant Examiner—Patricia A. Duffy
Attorney, Agent, or Firm—Benjamin Aaron Adler

[57] ABSTRACT

The present invention provides a method of identifying immunocompromised individuals who are at high risk for development of cryptococcosis, comprising the step of measuring the levels of IgG antibody to glucuronoxylomannan in the sera of said individuals. Also provided are various methods of detecting antibody to glucuronoxylomannan in sera and a kit for assaying the presence of antibody to glucuronoxylomannan in the sera of immunocompromised individuals.

7 Claims, 6 Drawing Sheets

METHOD TO IDENTIFY IMMUNOCOMPROMISED PATIENTS AT HIGH RISK FOR CRYPTOCOCCOSIS

BACKGROUND OF THE INVENTION

1. Field of the Invention

The present invention relates generally to the fields of immunology, infectious diseases and AIDS research. More specifically, the present invention relates to a novel method of identifying AIDS or other immunosuppressed patients at high risk for developing cryptococcosis.

2. Description of the Related Art

One of the remarkable features of the Acquired Immune Disease Syndrome (AIDS) is the fact that most deaths are not due to Human Immunodeficiency Virus (HIV) infection itself. In actuality, most deaths are caused by a variety of opportunistic protozoa, fungi, bacteria and viruses that would be of little consequence for normal, healthy individuals. The most common opportunistic infections include *Pneumocystis carinii*, *Toxoplasma gondii*, *Mycobacterium* spp, Human Cytomegalovirus and the yeast *Cryptococcus neoformans*.

*C. neoformans* is a yeast that is ubiquitous to our environment. It is likely that many individuals are infected with this yeast but their immune system prevents overt disease. Loss of immune function most likely leads to spread of the yeast from a previously latent site, probably from the lungs, to the blood and ultimately to the meninges.

Progress has occurred in the care of AIDS patients. Longevity has almost doubled and the quality of life for patients with AIDS has improved. A major advance in the treatment of patients with AIDS has been the prophylactic use of antibiotics for preventing pneumocystis pneumonia. A strategy in which all AIDS patients are given anti-pneumocystitis prophylaxis is effective because most (70%) patients with AIDS are expected to develop pneumocystis pneumonia.

Prophylactic treatment of cryptococcosis in patients with AIDS has great potential but the strategy must differ from the strategy used treat *Pneumocystis carinii*. Cryptococcosis is expected in 5–15% of AIDS patients. If only 5–15% of AIDS patients develop cryptococcosis, universal prophylactic treatment of AIDS patients for cryptococcosis is not realistic. Instead, prophylactic treatment of AIDS patients will depend on the development of a means to identify those AIDS patients at highest risk for cryptococcosis.

The prior art is deficient in the lack of effective means of identifying AIDS or other severely immunocompromised patients at highest risk for cryptococcosis. The present invention fulfills this longstanding need and desire in the art.

SUMMARY OF THE INVENTION

In one embodiment of the present invention, there is provided a method of identifying individuals who are at high risk for development of cryptococcosis, comprising the step of measuring the levels of antibody to glucuronoxylomannan in the sera of said individuals.

In another embodiment of the present invention, there is provided a method of coupling the polysaccharide gluconoxylomannan to a solid phase useful for the assay of antibody binding to an antigen, comprising the steps of activating the polysaccharide at a pH of about 8.5 using benzoquinone; coupling the activated polysaccharide to a hydrophobic ligand at about pH of 7.5; and binding of the modified GXM to said solid phase at a pH of about 7.0.

In another embodiment of the present invention, there is provided a method of detecting antibody to glucuronoxylomannan in sera comprising the steps of: incubating wells of an antigen-coated microtiter plate for 90 minutes at 25° C. with sera diluted in PBS-Tween; removing patient sera from the wells and washing said wells with PBS-Tween to remove unbound antibody; incubating washed wells for 30 minutes at 25° C. with diluted enzyme-conjugated antibody specific for human IgG; removing enzyme-conjugated antibody from the wells and removing unbound enzyme-conjugated antibody by washing the wells with PBS-Tween; adding substrate appropriate for the enzyme-conjugated antibody and incubating for 30 minutes at 25° C.; adding a stop solution and measuring the optical density of the enzyme product.

In yet another embodiment of the present invention, there is provided a kit for assaying the presence of antibody to glucuronoxylomannan in the sera of individuals at high risk for development of cryptococcosis, comprising a solid phase; a hydrophobic ligand that enables hydrophobic binding of glucuronoxylomannan to the solid phase; an enzyme indicator system; and substrate appropriate for the enzyme-linked antibody.

In still yet another embodiment of the present invention, there is provided a method of treating individuals who are at high risk for development of cryptococcosis, comprising the steps of: measuring the levels of antibody to glucuronoxylomannan in the sera of said individuals; and administering an anti-*Cryptococcis neoformans* agent.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A–1F show the effect of coating buffer formulation on binding of $^{125}$I-labeled tyraminated glucuronoxylomannan (T-GXM) to Immulon I plates. Data are presented as the amount of bound T-GXM after addition of various amounts of T-GXM (left panels) or as the percentage of added T-GXM that bound to the wells (right plates). T-GXM was diluted in 0.05M carbonate buffer (top panels), phosphate buffer (center panels), or citrate buffer (bottom panels). The buffers were either used unchanged (triangles), supplemented with 0.1M NaCl (squares) or supplemented with 0.95M NaCl (circles). Results shown are the mean of four replicate wells.

FIGS. 2A and 2B show the effect of incubation time and temperature on binding of T-GXM to Immulon I plates. Binding kinetics are plotted as the amount bound at each time interval (left panel) and as a pseudo first-order plot in which $A_o$ is the expected maximum amount of bound T-GXM and A is the available binding capacity at each time interval. Wells were incubated for various times at 4° (circles), 20° C. (squares) or 37° C. (triangles) with 100 ul of 10 ug/ml radiolabeled tyramylated GXM in phosphate coating buffer containing 0.95M NaCl. Results shown are the mean of three replicate wells.

FIG. 3 shows the effect of storage time and conditions on retention of T-GXM on Immulon I plates. Wells were coated with T-GXM and (i) washed with PBS-Tween and stored dry (circles), (ii) washed with PBS-Tween followed by a distilled water wash and stored dry (squares), or (iii) washed with PBS-Tween and stored with a PBS-Tween overlay (triangles). After the indicated storage time, all wells were washed with PBS-Tween, and the amount of bound T-GXM was determined. Results shown are the mean of four replicate wells.

DETAILED DESCRIPTION OF THE INVENTION

With reference to the present invention, the term "immunocompromised" means the loss in patients of T lymphocyte function such that the patients have increased susceptibility to disseminated cryptococcosis

*Cryptococcus neoformans* is an opportunistic yeast that is surrounded by a polysaccharide capsule. The primary structural component of the capsule is a polysaccharide, termed glucuronoxylomannan (GXM), which is composed of mannose, xylose, glucuronic acid, and O-acetyl groups. Anti-capsular and/or anti-GXM antibodies have a variety of biological activities including complement fixation, opsonization for phagocytosis by mouse resident peritoneal macrophages and human neutrophils, enhancement of anti-cryptococcal activity of human natural killer cells, and in vivo clearance of cryptococci via passive immunization.

Negatively charged capsular polysaccharides, such as crytococcal GXM, adhere poorly to the polystyrene plates typically used for solid-phase immunoassays. Prior art approaches reported to facilitate binding of polysaccharides to polystyrene and allow for measurement of anti-capsular antibodies include: (i) precoating plates with poly-L-lysine which forms multiple electrostatic bonds with negatively charged polysaccharides; (ii) covalent coupling of polysaccharides to poly-L-lysine which, in turn, binds to polystyrene plates; (iii) covalent coupling of polysaccharides to tyramine which greatly enhances adherence; (iv) complexing of negatively charged polysaccharides with positively charged methylated proteins; (v) covalent coupling of polysaccharides to solid phase derivitized proteins or coupling of polysaccharides to proteins followed by addition to polystyrene plates; (vi) biotinylation of polysaccharides with subsequent binding to avidin-coated plates; and (vii) direct passive binding of polysaccharides under coating conditions which facilitate immobilization.

Covalent coupling of polysaccharides to reagents which facilitate attachment typically involves activation of the polysaccharide for linkage to amino-containing compounds. Activation procedures include (i) treatment of polysaccharides with cyanogen bromide to introduce reactive groups, most likely imidocarbonates and cyanate esters, at the polysaccharide hydroxyl groups; (ii) limited periodate oxidation of polysaccharides to generate aldehyde groups that may be condensed with a suitable nucleophile; and (iii) treatment of polysaccharides with cyanuric chloride.

Benzoquinone activation has distinct advantages over alternative procedures such as cyanogen bromide activation because the activation can be accomplished at a pH ≦8.5. Cryptococcal polysaccharide is decorated with O-acetyl groups that are readily hydrolyzed by the more alkaline pH required for cyanogen bromide activation or the alkaline pH produced by sodium borohydride which is typically used when periodate-oxidized polysaccharide is coupled to amino groups. The present invention incorporates coupling of tyramine to benzoquinone-activated polysaccharide and defines conditions which favor binding of tyraminated GXM (T-GXM) to polystyrene or polyvinyl chloride microtiter plates.

The present invention illustrates: (i) a characterization of the frequency and immunoglobulin class of anti-GXM antibodies among a group of normal adult volunteers; (ii) a determination of the subclass of IgG antibodies found in the sera of normal volunteers; and (iii) a determination that the progression from HIV infection to AIDS is accompanied by quantitative and qualitative effects on production of anti-GXM antibodies. The present invention shows that some normal subjects have high levels of anti-GXM IgG and essentially all subjects have readily detectable anti-GXM IgM. The anticapsular IgG is primarily of the IgG2 subclass with IgG1 antibodies occurring in the sera of some individuals. Finally, the progression of HIV infection to AIDS is accompanied by a selective loss of anti-GXM antibodies of the IgM class; however, there is little or no loss of anti-GXM antibodies of the IgG class.

In the present invention, there is provided a method of identifying individuals who are at high risk for development of cryptococcosis, comprising the step of measuring the levels of antibody to glucuronoxylomannan in the sera of said individuals. Further provided is a method of treating individuals who are at high risk for development of cryptococcosis, comprising the steps of: measuring the levels of antibody to glucuronoxylomannan in the sera of said individuals; and administering an anti-*Cryptococcis neoformans* agent.

Clearly, the methods of the present invention, although applicable in any individual, are most desirable in individuals who are immunocompromised and, therefore, at risk for development of cryptococcosis. Generally, the methods of the present invention may be performed on any immunocompromised person with deficient or suppressed T lymphocyte function. One class of immunocompromised individuals are individuals infected with the Human Immunodeficiency Virus. An additional group of immunocompromised individuals are those in a pathophysiological state selected from the group consisting of the Acquired Immune Deficiency Syndrome, use of supraphysiologic doses of adrenal corticosteroids, sarcoidosis and lymphoma. Generally, the methods of the present invention measure the levels of antibody to glucuronoxylomannan in the sera of selected individuals. Preferably, the antibody measured is an IgG.

The present invention also provides a kit for assaying the presence of antibody to glucuronoxylomannan in the sera of immunocompromised individuals comprising, a solid phase; a hydrophobic ligand that enables hydrophobic binding of GXM to the solid phase; an enzyme indicator system; and a substrate appropriate for the enzyme-linked antibody.

In the use of the kit provided by the present invention, cryptococcal glucuronoxylmannan is immobilized to a solid phase such that GXM is firmly bound to the solid phase without modifying, blocking or degrading epitopes recognized by anticryptococcal antibody. Generally, the solid phase may be any that binds the GXM. Preferably, the solid phase is polystyrene or polyvinyl chloride microtiter plates; alternate solid phases are nitrocellulose or other forms of paper, magnetic beads or plastic dip sticks.

The preferred manner of immobilization is coupling of the GXM to a hydrophobic ligand that enables hydrophobic binding of GXM to the solid phase. The hydrophobic ligand should not be recognized by antibodies that occur in human serum. Tyramine is the preferred ligand. Coupling of GXM to the hydrophobic ligand must be covalent and done in a manner that does not permit hydrolysis of the alkaline sensitive O-acetyl side chains. The optimal concentration of the antigen, the optimal pH for coating of microtiter plates, and the optimal temperature for coating will all be readily recognizable to those having skill in the art after having the benefit of the disclosure of the present invention.

The kit of the present invention also contains an enzyme indicator system such as antibodies specific for human IgG heavy chains. Preferably, the antibodies are horseradish peroxidase-labeled goat (or sheep) antibodies. Other enzyme indicator systems are well known in the art. Generally, a substrate appropriate for the enzyme-linked antibody is included. A representative example of such a substrate is 3,3', 5,5'-tetramethyl benzidine and hydrogen peroxide (TMB Microwell Peroxide Substrate System). A person with ordinary skill in this art would recognize suitable alternatives.

The present invention further provides a method of detecting antibody to glucuronoxylomannan in sera comprising the steps of: incubating wells of an antigen-coated microtiter plate for 90 minutes at 25° C. with sera diluted in PBS-Tween; removing patient sera from the wells and washing said wells with PBS-Tween to remove unbound antibody; incubating washed wells for 30 minutes at 25° C. with diluted enzyme-conjugated antibody specific for human IgG; removing enzyme-conjugated antibody from the wells by washing with PBS-Tween; adding substrate appropriate for the enzyme-conjugated antibody and incubating for 30 minutes at 25° C.; and adding a stop solution and measuring the optical density of the enzyme product.

As a control for nonspecific binding, an aliquot of the human serum is pre-incubated with 4 µg/ml GXM prior to incubation with the antigen-coated wells. The antigen-neutralized patient serum is then incubated with an antigen immobilized on a solid phase in the manner described above.

The following examples are given for the purpose of illustrating various embodiments of the invention and are not meant to limit the present invention in any fashion.

EXAMPLE 1

*Cryptococcal glucuronoxylomannan*

Cryptococcal GXM was isolated by a modification of the procedure described by Cherniak et al., *Infect. Immun.* 59:59 (1991). Briefly, *C. neoformans* serotype A strain 24064 (American Type Culture Collection, Rockville, Md.) was grown in a liquid synthetic medium on a gyratory shaker at 100 rpm for four days at 30° C. The yeast cells were killed by addition of formaldehyde to a final concentration of 1%. Sodium acetate crystals and glacial acetic acid were added to final concentrations, respectively, of 10% and 1%, and the yeast cells were removed by centrifugation at 10,000× g. The polysaccharide was precipitated from the supernatant fluid by addition of 2.5 volumes of 95% ethanol, and the precipitate was collected by centrifugation. The polysaccharide precipitate was dissolved at a concentration of approximately 5 mg/ml in 0.2M NaCl, and the solution was clarified by centrifugation. Hexadecyltrimethylammonium bromide (CTAB) was added (3 mg CTAB/mg polysaccharide), and two volumes of 0.05% CTAB were added slowly with stirring. The GXM-CTAB complex was collected by centrifugation and redissolved at approximately 5 mg/ml in 0.2M NaCl. The polysaccharide was reprecipitated with ethanol and CTAB as described above. Finally, the polysaccharide was precipitated with ethanol, dialyzed against deionized water and lyophilized.

EXAMPLE 2

Coupling of tyramine to GXM

GXM was covalently linked to tyramine using several modifications of the benzoquinone activation procedure described by Kozel and Hermerath, *J. Immunol. Meth.*, 107:53 (1988) and *Infect. Immun.* 43:879 (1984). GXM was dissolved in deionized water (10 mg/ml) and mixed with an equal volume of 0.2M sodium bicarbonate (pH 8.5). Benzoquinone (0.25 volumes, 250 mM in absolute ethanol) was added to produce a final concentration of 50 mM benzoquinone in 20% ethanol and incubated with the GXM for 60 minutes at room temperature. The pH must not be above 8.5 or the incubation time extend beyond 60 minutes because the O-acetyl groups on the polysaccharide may be lost through alkaline hydrolysis. Sodium acetate crystals (10% w/v) and glacial acetic acid (1% v/v) were added, and the GXM was precipitated by addition of two volumes of 95% ethanol. The precipitate was collected by centrifugation, dissolved in acetate buffer (10% sodium acetate crystals and 1% glacial acetic acid) at a concentration of approximately 2 mg GXM/ml and reprecipitated by addition of two volumes of ethanol. The precipitate was collected by centrifugation and dissolved at a concentration of approximately 4 mg GXM/ml in 0.1M sodium phosphate (pH 7.5) containing 0.5M NaCl. The GXM was dialyzed against the same buffer and against 0.1M sodium phosphate (pH 7.5).

Benzoquinone-activated GXM was coupled to tyramine by mixing the activated polysaccharide (approximately 2 mg/ml) with an equal volume of tyramine hydrochloride (1 mg/ml in 0.1M sodium phosphate, pH 7.5) and the mixture was incubated overnight at room temperature. Sodium acetate crystals and glacial acetic acid were added as above, and the tyraminated GXM was precipitated by addition of two volumes of 95% ethanol. The precipitate was collected by centrifugation, dissolved at a concentration of approximately 4 mg/ml in 0.1M sodium phosphate (pH 7.5) containing 0.5M NaCl, and dialyzed sequentially against 0.1M sodium phosphate (pH 7.5) containing 0.5M NaCl and 0.1M sodium phosphate (pH 7.5). The GXM concentration was determined by the phenol-sulfuric acid assay, and the tyramine-coupled GXM was diluted to 2 mg/ml, sterilized by filtration, and stored at 4° C.

The extent of tyramination of the GXM was determined by measuring the optical density at 280 nm using tyramine hydrochloride as a standard and benzoquinone-activated polysaccharide as the blank. Approximately 30 moles of tyramine were bound to each mole of GXM, assuming a molecular weight of 500,000 for cryptococcal GXM.

EXAMPLE 3

Assay for binding of T-GXM to styrene plates

Tyraminated GXM was labeled with $^{125}$I by the Iodogen (Pierce Chemical Co., Rockford, Ill.) procedure. Radiolabeled GXM was separated from free iodine by filtration through Sephadex G-25. Typically, 0.4 mg of GXM was labeled to a specific activity of $3.0 \times 10^6$ cpm/ug. $^{125}$I-labeled GXM was mixed with unlabeled GXM to produce a specific activity of $2.5 \times 10^5$ cpm/ug GXM.

The incubation conditions used for binding of T-GXM to the plates varied with the experimental protocol. After the coating step, the plates were washed six times with PBS-Tween (8 g NaCl, 0.2 g $KH_2PO_4$, 2.9 g $Na_2HPO_4.12H_2O$, 0.2 g KCl and 0.5 ml Tween 20 per liter deionized $H_2O$). The wells were separated and the amount of bound GXM was determined with a gamma counter. Statistical comparisons of the amount of binding of GXM under various conditions were made with a t-test using $P<0.05$ as the criterion for statistical significance.

EXAMPLE 4

Optimal conditions for immobilization of T-GXM

To illustrate the importance of pH and ionic strength in binding of T-GXM to Immulon I plates, T-GXM was prepared in concentrations ranging from 625–20,000 ng/ml in (i) 0.05M carbonate buffer, pH 9.6; (ii) 0.05M sodium phosphate, pH 7.0, with 10 mM EDTA; or (iii) 0.05M citrate, pH 4.5. The coating buffers were used (i) unchanged, (ii) with NaCl added to 0.1M, or (iii) NaCl added to 0.95M. Plates were incubated with the T-GXM overnight at room temperature. The wells were washed to remove unbound T-GXM, and the amount of adsorbed T-GXM was determined. The data were calculated as nanograms T-GXM bound/well and as the percentage of GXM added that bound to the wells.

Figure 1:
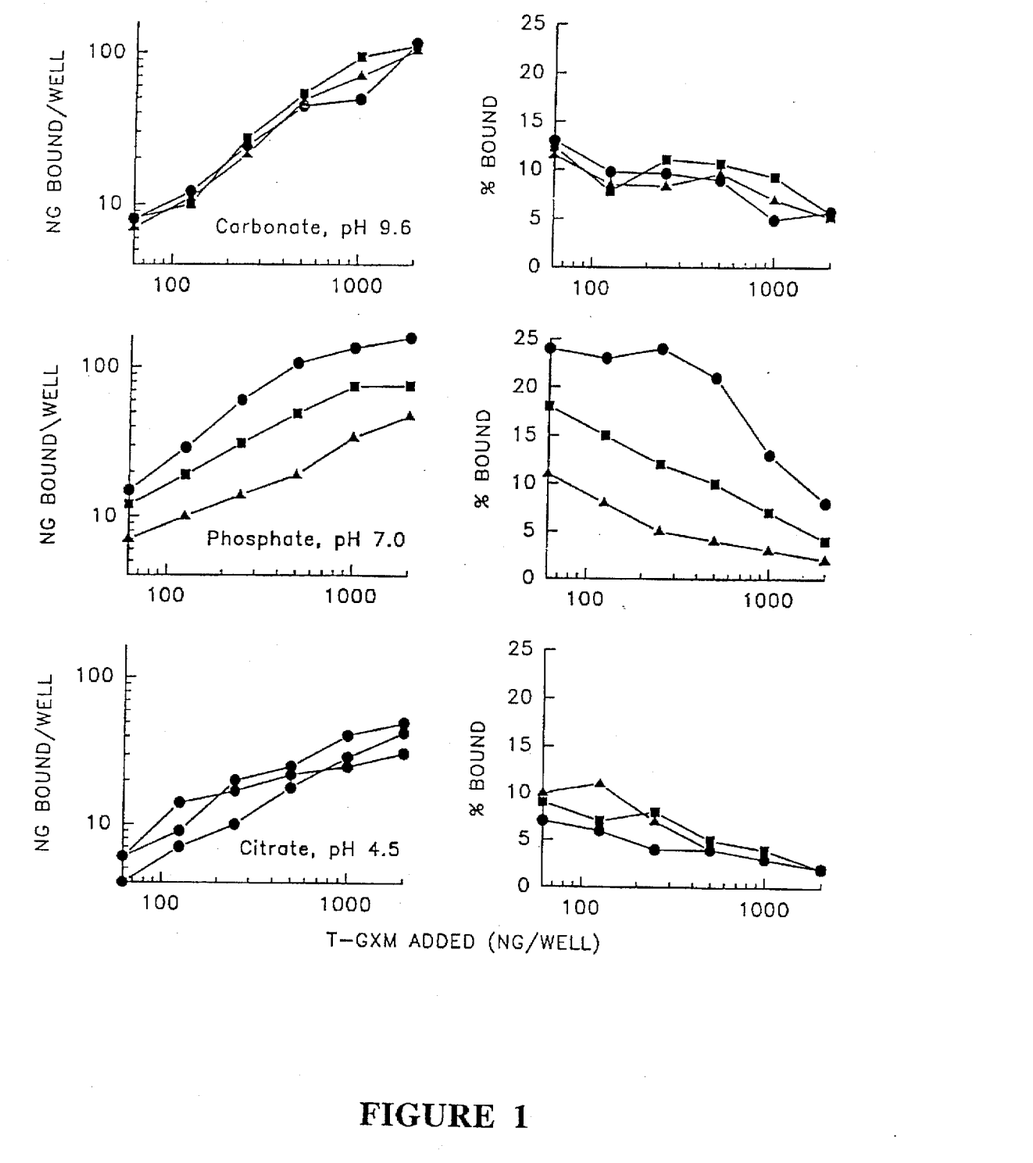

FIG. 1 shows that appreciable amounts of GXM bound when incorporated into either the carbonate or phosphate buffers. Maximum binding in the carbonate and phosphate buffers was approximately 100–150 ng/well. Use of the citrate buffer produced a substantial reduction in the amount of binding, with maximum observed binding of approximately 50 ng/well. Incorporating NaCl to 0.1M significantly enhanced the binding that occurred with the phosphate buffer over binding in the same buffer without additional NaCl. Similarly, significantly more binding occurred in the phosphate buffer with 0.95M NaCl than occurred using the same buffer with 0.1M NaCl. Increased ionic strength did not have a consistent enhancing effect on binding in the carbonate or citrate buffers.

EXAMPLE 5

Time and temperature requirements

The effects of coating time and temperature were examined. Wells of Immulon I plates were incubated with 100 µl of 10 µg/ml radiolabeled T-GXM in phosphate coating buffer containing 0.95M NaCl. The plates were incubated for 1, 2, 4, 8, 24, or 48 hours at 4° C., 20° C. or 37° C. The plates were washed, and the amount of bound T-GXM was determined.

Figure 2:
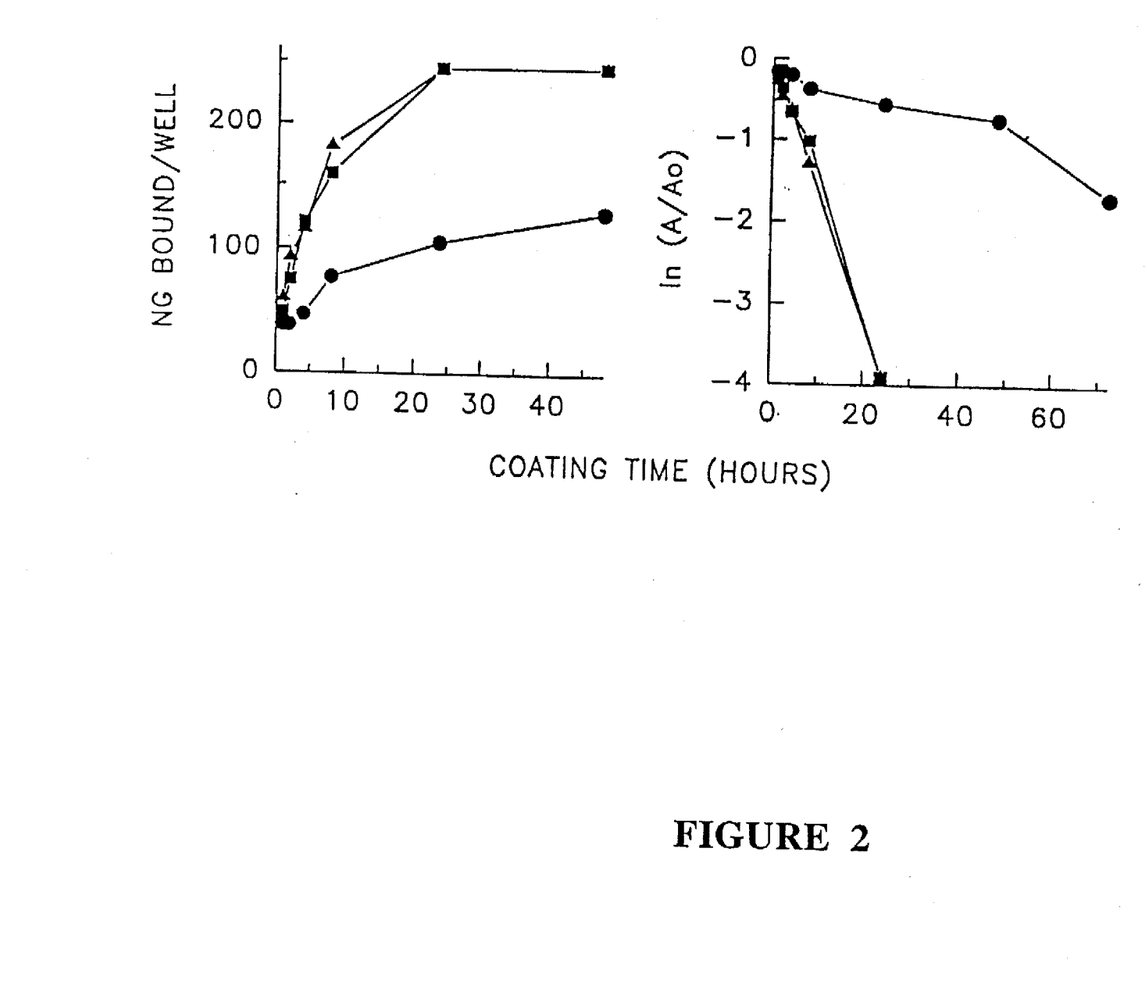
Figure 3:
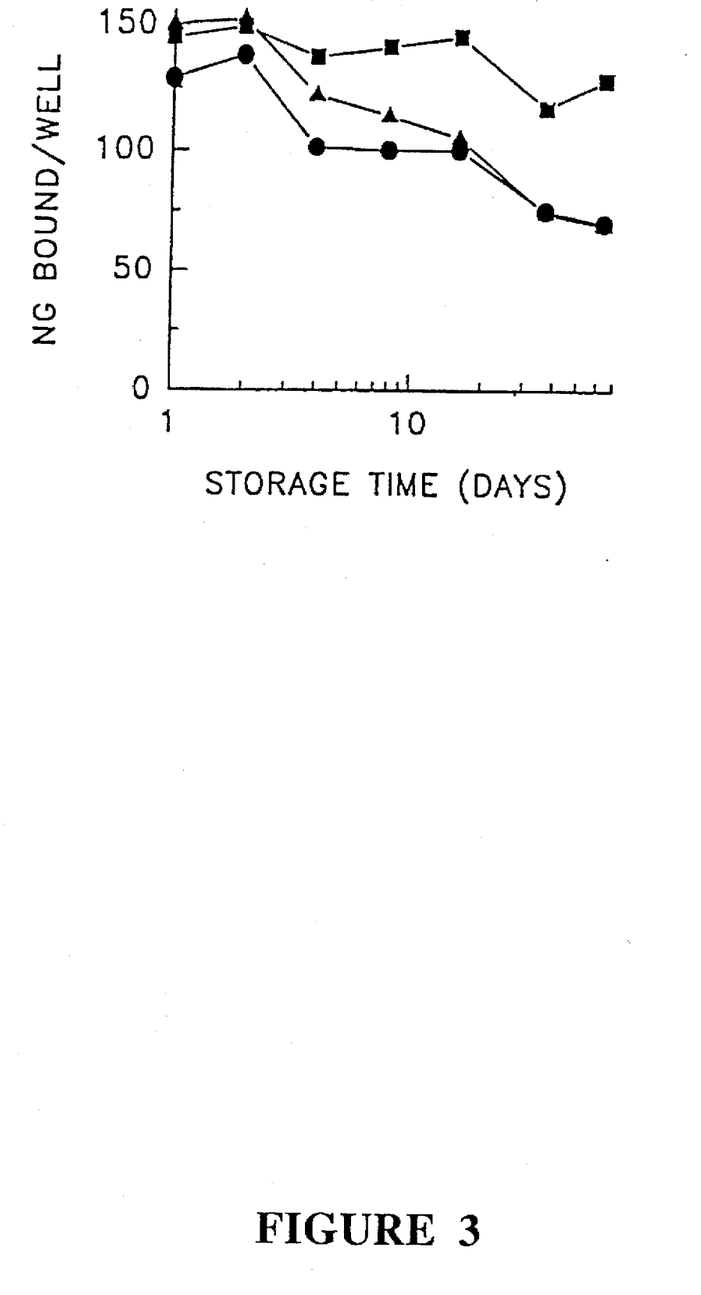

FIG. 2 showed that there was no appreciable difference in levels of binding at 20° C. or 37° C. at any coating time that was examined. Incubation of plates for 48 hours at 20° C. or 37° C. produced no significant additional binding beyond that observed at 24 hours. Incubation of plates at 4° C. produced significantly less binding than occurred when plates were coated at 20° C. or 37° C. at all incubation times $\geq 2$ hours. On this basis, coating of plates with T-GXM for 24 hours at 20° C. was used subsequently.

A plot of ln $(A/A_o)$ vs time (FIG. 2), where A is the vacant binding capacity at any given time and $A_o$ is the total binding capacity (defined here as the amount of bound T-GXM when incubated for 48 hours at 20° C. or 37° C.) was linear for plates coated at 0° C., 20° C. or 37° C. This suggested that binding occurs at a single first order rate constant characteristic of each coating temperature. Binding was much slower at 4° C. (pseudo first-order rate constant$\approx 3.2 \times 10^{-4}$) than binding at either 20° C. (pseudo first order rate constant$\approx 2.7 \times 10^{-3}$) or 37° C. (pseudo first-order rate constant$\approx 2.6 \times 10^{-3}$).

EXAMPLE 6

Stability of T-GXM immobilization on polystyrene plates

A variety of eluting and dissociating agents were examined in an effort to assess stability of the binding of T-GXM to Immulon I plates. Wells were coated for 24 hours at room temperature with 100 µl of 10 ug/ml radiolabeled T-GXM in phosphate coating buffer containing 0.95M NaCl. The wells were washed six times with PBS-Tween, and 100 µl of eluting agent was added to each well and incubated 1 hour at 20° C. The wells were washed six times with PBS-Tween and the amount of bound tyraminated GXM was determined. The results are presented as the percentage of tyraminated GXM removed relative to wells treated with PBS.

TABLE I showed that bound tyraminated GXM was remarkably resistant to elution with most dissociating agents. Significant elution occurred when wells were treated with alkaline buffers or chaotropic salts. However, the amount of T-GXM eluted from the plates never exceeded 35% over that observed with plates incubated with PBS.

The stability of immobilized T-GXM was determined after a variety of storage conditions. Wells of polystyrene plates were coated for 24 hours at room temperature with 100 µl of 10 µg/ml radiolabeled T-GXM in phosphate coating buffer containing 0.95M NaCl. The wells were washed with PBS-Tween, and (i) the PBS-Tween was removed and the plates were stored dry, (ii) the plates were washed two additional times with distilled water and stored dry, or (iii) the plates were stored with an overlay of 100 µl PBS-Tween. Four wells were removed at various time intervals, washed with PBS-Tween, and the amount of bound tyraminated polysaccharide was determined. There was a gradual loss of T-GXM from plates that were either stored dry after the PBS-Tween wash (half life$\approx$46 days) or stored with a PBS-Tween overlay (half life$\approx$47 days). Removal of the PBS-Tween by washing with distilled water enabled the plates to be stored dry with little loss of bound T-GXM after the 64 day storage time (estimated half life >1000 days).

TABLE I

Elution of T-GXM from wells of polystyrene plates.

| Eluting Agent | pH | Percentage GXM eluted[a] | P vs PBS |
|---|---|---|---|
| Glycerol (35%) | 8.0 | 1 ± 11 | 0.83 |
| Glycine, 0.5 M HCl, 0.5 M NaCl | 2.0 | −5.2 ± 8.0 | 0.26 |
| Guanidine thiocyanate, 6.0 M, 0.05 M Hepes/NaOH | 7.2 | 19 ± 3 | <0.001 |
| Guanidine hydrochloride, 6.0 M, 0.05 M Hepes/NaOH | 7.2 | 22 ± 5.6 | <0.001 |

TABLE I-continued

Elution of T-GXM from wells of polystyrene plates.

| Eluting Agent | pH | Percentage GXM eluted[a] | P vs PBS |
|---|---|---|---|
| H$_2$O | nd[b] | 1.9 ± 12 | 0.75 |
| MgCl$_2$·H$_2$O (4.0 M), 0.1 M Hepes/NaOH | 6.3 | 9.2 ± 3.4 | 0.02 |
| MgCl$_2$·H$_2$O,3.0 M, 0.075 M Hepes /NaOH, 25% ethylene glycol | 7.2 | 8.3 ± 7.8 | 0.083 |
| Na$_2$CO$_3$ (1.0 M), 0.5 M NaCl | 11.6 | 31 ± 8.4 | <0.001 |
| NaCl (3.0 M) | nd | 11 ± 14 | 0.13 |
| NaI (4.0 M) | 7.6 | 33 ± 11 | <0.001 |
| NH$_4$OH (1.0 M) | 11.5 | 18 ± 5.7 | <0.001 |
| PBS-0.01% Tween | 7.0 | 10 ± 11 | 0.10 |
| PBS-1% SDS | 7.0 | 2.2 ± 6.2 | 0.47 |
| Sodium thiocyanate, 6.0 M, 0.05 M Hepes/NaOH | 7.2 | 19 ± 8.1 | 0.003 |
| Urea, 8.0 M, 0.05 M Tris/HCl | 8.0 | 9.2 ± 17 | 0.66 |

[a]Elution calculated as the amount of T-GXM removed by each eluting agent compared to PBS alone. Data are reported for the mean of five replicate wells ± SD.
[b]Not determined.

Activation of capsular polysaccharides for coupling to tyramine has been accomplished by use of CNBr, cyanuric chloride, and periodate oxidation. The present invention shows that activation with benzoquinone is also an effective means for tyramination of polysaccharides for use in immunologic assays. There are several characteristics of benzoquinone relevant to the activation procedure. First, benzoquinone activation is made at a lower pH (≦8.5) than is required by alternative procedures. This is of particular importance with cryptococcal polysaccharide because O-acetylation is an important component of the antigenic character of GXM. The O-acetyl groups are readily lost from the polysaccharide at pH >8.5. Secondly, benzoquinone activation introduces a chromophore into the polysaccharide which facilitates monitoring of the activation procedure.

The amount of T-GXM binding to polystyrene plates compares well with binding observed with proteins. Saturation of binding sites by T-GXM coated in phosphate buffer containing 0.95M NaCl began to occur at 50–100 ng/cm$^2$. The differences in results obtained with proteins and T-GXM are readily explained by the highly hydrated nature of GXM. The fact that polysaccharides are highly hydrated predicts that lesser amounts of polysaccharide will be required on a gravimetric basis to fill all available sites.

Temperature can be an important factor in the efficiency with which T-GXM binds to polystyrene. The pseudo first order rate constant for binding at 4° C. was approximately eight times lower than rate constants for binding at either 20° C. or 37° C.

The present invention illustrates that T-GXM binds to polystyrene with a remarkable tenacity. Few eluting agents were able to accomplish any significant removal of T-GXM from the plates. The strength of binding allowed for long term storage of the plates with little loss of bound T-GXM. Introduction of the tyramine group undoubtedly makes the molecule more hydrophobic with an accompanying greater attraction to polystyrene. However, with approximately 30 moles of tyramine per mole of GXM, the multivalent nature of binding by individual GXM molecules is probably a significant factor in the strength of the binding. Unlike a protein in which many of the hydrophobic moieties are located in the interior of the molecule, it is likely that the extended nature of the GXM allows most, if not all, of the tyramine groups to bind to the polystyrene surface.

EXAMPLE 7

Cryptococcal cells and GXM

GXM was isolated as described in Examples 1 and 2. GXM was covalently linked to tyramine as described in Example 2.

Benzoquinone-activated GXM was coupled to tyramine by mixing the activated polysaccharide (approximately 4 mg/ml) with an equal volume of tyramine hydrochloride (1 mg/ml in 0.1M sodium phosphate, pH 7.5) and incubated overnight at room temperature. Sodium acetate crystals and glacial acetic acid were added as above, and the tyramine-coupled GXM was precipitated by addition of two volumes of 95% ethanol. The precipitate was collected by centrifugation, dissolved at a concentration of approximately 4 mg/ml in 0.1M sodium phosphate (pH 7.5) containing 0.5M NaCl, and dialyzed sequentially against 0.1M sodium phosphate (pH 7.5) containing 0.5M NaCl and 0.1M sodium phosphate (pH 7.5). The GXM concentration was determined by the phenol-sulfuric acid assay as described by Dubois, et al., Anal. Chem. 28:350–356 (1956), and the tyramine-coupled GXM was diluted to 2 mg/ml, sterilized by filtration, and stored at 4° C.

EXAMPLE 8

ELISA assays for anticryptococcal antibody

Wells of Immulon I microtiter plates (Dynatech Laboratories, Inc., Chantilly, Va.) were coated overnight at 4° C. with 100 ng tyraminated GXM (T-GXM) in 100 µl coating buffer (0.05M sodium phosphate, pH 7.4, containing 10 mM EDTA). The wells were washed three times with blocking buffer (0.05M sodium phosphate, pH 7.4) and blocked for 90 minutes with 300 µl of 0.05% Tween 20 in blocking buffer. Plates coated with tyraminated GXM were washed three times with PBS-Tween (PBS containing 0.05% Tween 20) and incubated for 90 minutes with serial two-fold dilutions of human serum in PBS-Tween, beginning with a 1:5 dilution. As a negative control, all sera were diluted in PBS-Tween containing 4 µg GXM/ml and incubated for 30 minutes prior to addition to wells coated with tyraminated GXM (GXM neutralized serum). After incubation with serum or GXM-neutralized serum, the wells were washed three times with PBS-Tween and incubated for 90 minutes at room temperature with horseradish peroxidase (HRPO)-labeled second antibody.

The second antibodies were HRPO-labeled, affinity purified goat antihuman IgG heavy chains (1/16,000; Southern Biotechnology, Cat. no. 2040-05), HRPO-labeled, affinity purified goat anti-human IgM heavy chains (1/15,000; Southern Biotechnology, Cat. no. 2020-05), HRPO-labeled, affinity purified goat anti-human IgA heavy chains (1/12,000; Southern Biotechnology, Cat. no. 2050-05), HRPO-labeled, affinity purified goat anti-human kappa (1/10,000; Southern Biotechnology, Cat. no. 2060-05) or HRPO-labeled, affinity purified anti-human lambda (1/5000; Southern Biotechnology, Cat. no. 2070-05). The second antibody was used at eight times the dilution of antibody producing an OD$_{450}$ of 2.5 with wells coated with purified IgG (anti-IgG, anti-kappa, or anti-lambda), IgM (anti-IgM), or IgA (anti-IgA). The plates were washed three times with PBS-Tween and incubated for 30 minutes with 100 µl TMB Microwell Peroxidase Substrate Solution (Kirkegaard & Perry Labs, Inc., Gaithersburg, Md.). The reaction was stopped by addition of 100 µl 1M H$_3$PO$_4$. The absorbance was read within 30 minutes at 450 nm with a Ceres 900 enzyme immunosorbent assay workstation (Bio-Tek Instruments, Inc., Winooski, Vt.). All ELISA assays were done in duplicate, including the GXM-neutralized control. Averages were calculated from duplicate wells, and the specific $OD_{450}$ was calculated by subtracting the $OD_{450}$ obtained from the GXM-neutralized serum from the $OD_{450}$ obtained when sera were not preincubated with GXM. The data were analyzed with Kineticalc EIA Application Software Version 2.12 (Bio-Tek Instruments, Inc.) in a titer mode. The best fit for the data was determined with the 4-parameter algorithm, and the titer threshold was set at 0.5. Under these conditions, the serum dilution producing an $OD_{450}$, corrected for background (GXM-neutralized), of 0.5 was reported as the endpoint. Sera with an $OD_{450}$ less than 0.5 at a serum dilution of 1/5 were reported as negative. Using a murine monoclonal IgG1 antibody as a standard, approximately 500 pg of antibody produced an $OD_{450}$ of 0.5.

The ELISA assay described above was modified to determine the IgG subclass of anti-GXM IgG antibody. In this modified assay, plates were coated with GXM and incubated with serum dilutions or serum diluted in PBS-Tween containing GXM as described above. The wells were washed and incubated for 90 minutes at room temperature with optimally diluted murine monoclonal antibodies specific for human IgG1 (1/2000; Calbiochem, La Jolla; Cat no. 411451), IgG2 (1/8000; Calbiochem; Cat no. 411461), IgG3 (1/40,000; Calbiochem; Cat no. 411481), or IgG4 (1/1500; Calbiochem; 411492 ). The plates were then washed with PBS-Tween, incubated with 100 µl of peroxidase-labeled goat anti-mouse IgG (1/4500; Southern Biotechnology Assoc., Inc.; Cat. no. 1 030-05), washed, and incubated with substrate as above. Results are reported as the serum dilution, corrected for background (GXM-neutralized), that produced an $OD_{450}$ of 0.5.

EXAMPLE 9

Figure 4:
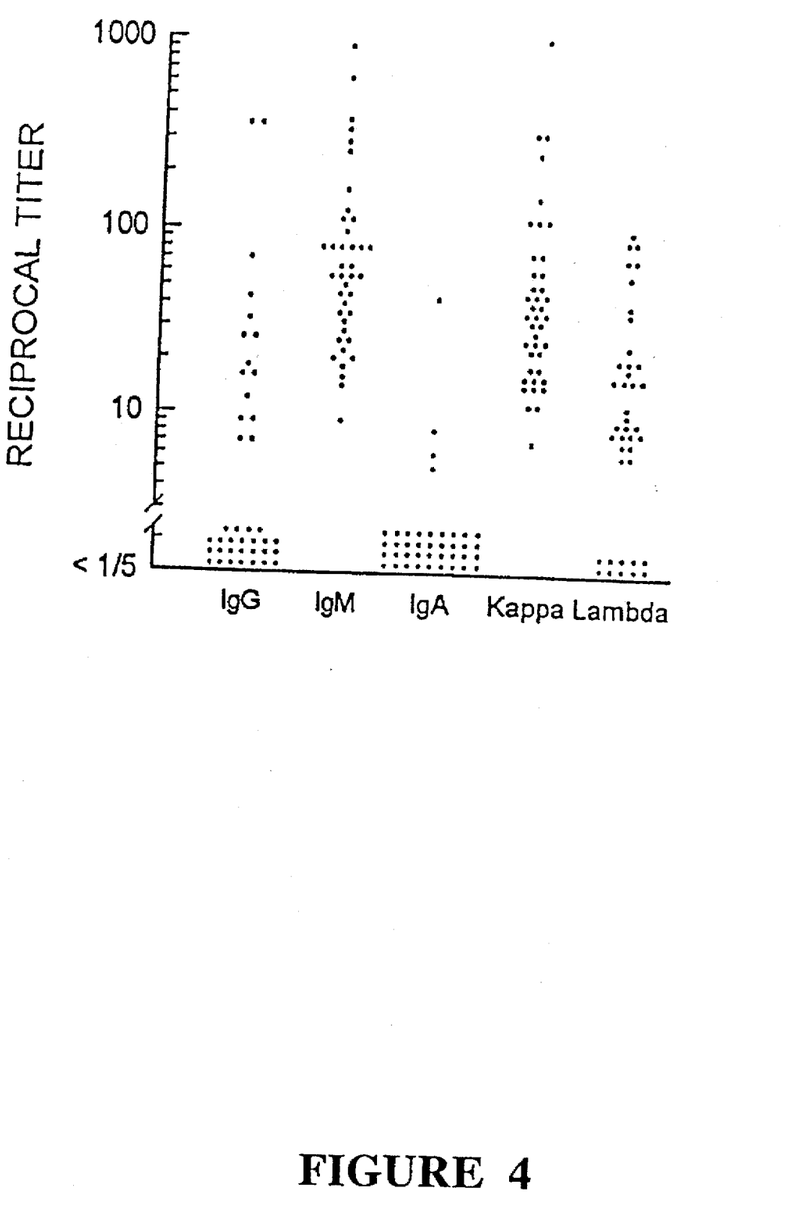
FIG. 4 shows the Anti-GXM antibodies in sera from 40 normal adult donors. Each point represents an individual serum sample assayed for antibodies with IgG, IgM or IgA heavy chains or kappa or lambda light chains.

Occurrence and immunoglobulin class of anti-GXM antibodies in sera from normal donors Sera were examined to determine the levels of antibodies of the IgG, IgM, and IgA classes. Serum was obtained from 40 normal adult volunteers. The sera were also examined to assess the occurrence and levels of antibodies with kappa or lambda light chains. FIG. 4 shows that 28% of the sera had IgG antibodies with titers $\geq 1/10$, 98% had IgM antibodies with titers $\geq 1/10$, and only one serum sample had IgA antibodies with a titer $\geq 1/10$. Ninety eight percent had antibodies with kappa chains with titers $\geq 1/10$, and 45% had antibodies with lambda chains with titers $\geq 1/10$.

Figure 5:
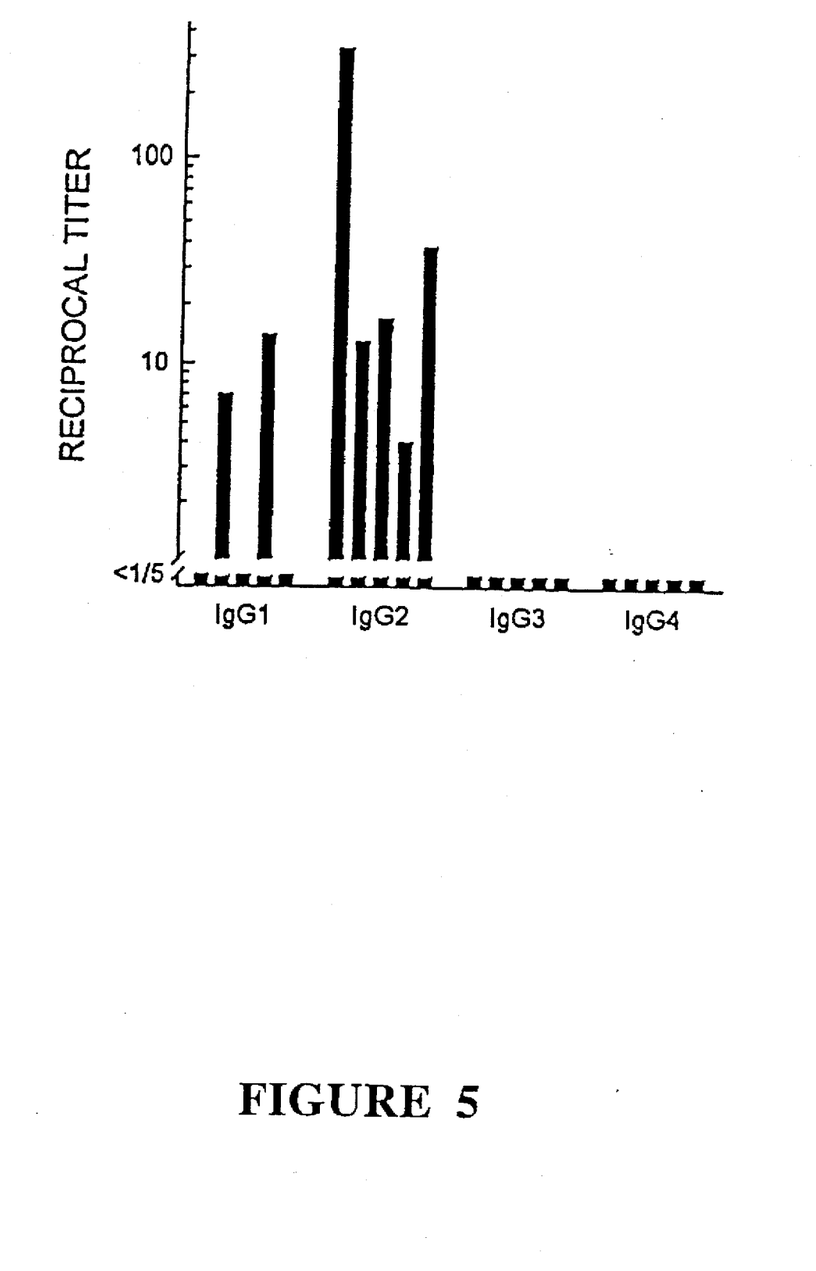
FIG. 5 shows the assay of normal human serum for anti-GXM antibodies of the IgG1, IgG2, IgG3, and IgG4 subclasses. Sera chosen for analysis had anti-GXM IgG antibody titers ≧ 1/50.

Five sera having IgG antibody titers $\geq 1/50$ were examined further to determine the IgG subclass of the anti-GXM IgG. The results (FIG. 5) showed that each of the sera contained detectable levels of anti-GXM antibody of the IgG2 subclass. Two of the sera also contained detectable levels of IgG1 antibody. None of the sera contained detectable levels of anti-GXM antibody of the IgG3 or IgG4 subclasses.

EXAMPLE 10

Characteristics of anti-GXM antibodies in sera from HIV-positive donors

The frequency of occurrence and levels of anti-GXM antibodies with various heavy and light chain isotypes in sera of patients was examined who were i) HIV-positive with CD4 counts $\geq 500$ cells/µl, ii) HIV-positive with CD4 counts of 200–499 cells/µl, and iii) HIV-positive with CD4 counts <200 cells/µl. Positive titers were defined as antibody titers $\geq 1/10$.

Figure 6:
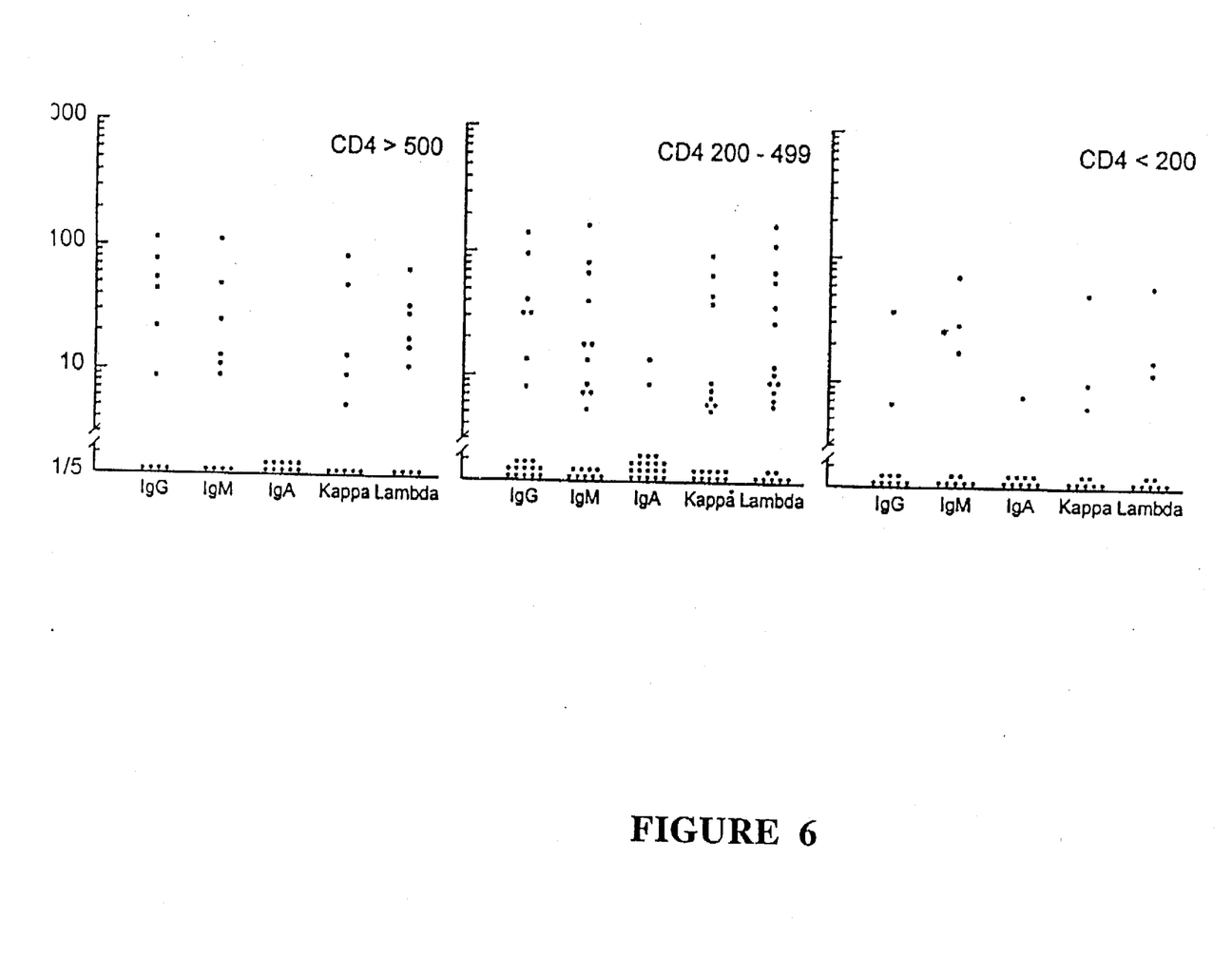
FIGS. 6A–6C show the occurrences and characteristics of anti-GXM antibodies in sera obtained at various stages in the progression from HIV infection to AIDS. Sera were obtained from 10 subjects who were HIV positive with CD4 counts>500/µl (left panel), 20 subjects with CD4 counts of 200–499/µl (center panel), and 10 subjects with CD4 counts<200/µl (right panel).

FIG. 6 shows the results from analysis of sera from HIV-positive donors. A comparison of the frequency of positive titers among normal donors (FIG. 4) and HIV-positive donors (FIG. 6) is presented in TABLE II. There is less frequent occurrence of anti-GXM IgG in patients with CD4 levels below 200. However, this difference was not significantly different. Anti-GXM of the IgM class was significantly more frequent among normal subjects than among HIV-positive donors, regardless of CD4 levels. Similarly, anti-GXM antibodies with kappa light chains were significantly less frequent among HIV-positive donors than among normal subjects. It is possible that other differences might have been noted if actual antibody levels were compared rather than the frequency of subjects with titers $\geq 1/10$. As a consequence, individual titers in the various subject groups were compared by the Mann-Whitney rank sum test. With one exception, significant differences as determined by this latter test were exactly as found when the data were evaluated in terms of the frequency of positive titers. The exception was a significant ($p \leq 0.01$) depression (relative to normal subjects) in titers of antibodies with lambda light chains found in sera from HIV-positive patients with CD4 levels below 200.

TABLE II

Anti-GXM antibodies of various immunoglobulin classes in sera from normal donors or HIV-positive individuals with differing CD4 levels

| Antibody class | Normal serum Positive[1]/total | HIV positive, CD4 > 500 Positive/total | P vs normal[2] |
|---|---|---|---|
| IgG | 11/40 | 5/10 | =0.27 |
| IgM | 39/40 | 5/10 | <0.001 |
| IgA | 1/40 | 0/10 | >0.99 |
| Kappa | 39/40 | 3/10 | <0.001 |
| Lambda | 19/40 | 6/10 | =0.51 |

| Antibody | HIV positive, CD4 200–499 Positive/total | P vs normal | HIV positive, CD4 < 200 Positive/total | Pvs normal |
|---|---|---|---|---|
| IgG | 6/20 | >0.99 | 1/10 | =0.42 |
| IgM | 7/20 | <0.001 | 4/10 | <0.001 |
| IgA | 1/20 | >0.99 | 0/10 | >0.99 |
| Kappa | 2/20 | <0.001 | 1/10 | <0.001 |
| Lambda | 8/20 | =0.78 | 5/10 | >0.99 |

[1] Sera with class specific antibody titers $\geq 1/10$ were classified as positive.
[2] Statistical analysis by Fisher Exact Test.

EXAMPLE 11

Retrospective analysis of AIDS patient's sera

The present invention provides a highly sensitive assay for detection of antibodies reactive with the major capsular polysaccharide of *Cryptococcus neoformans*. The methods of the present invention determine the presence of a latent infection because this yeast leaves an immunological "footprint" in the form of IgG antibody that is reactive with the polysaccharide. Thus, the presence of antibody signals the presence of a latent cryptococcal infection and, therefore, high risk for cryptococcosis in patients with AIDS.

Assay for antibody

Sera is evaluated for the presence of antibody to glucuronoxylomannan, the major serotype specific polysaccharide of *C. neoformans*. The polysaccharide is the primary constituent of the capsular polysaccharide that surrounds the yeast. Antibody to GXM is evaluated in an enzyme immunosorbent assay in which the GXM is immobilized on standard microtiter plates. Immobilization requires chemical modification of the GXM in a manner that preserves the antigenic structure of the polysaccharide while increasing hydrophobicity needed for strong attachment to the plates. The assay uses a benzoquinone coupling procedure that allows for binding of tyramine to the GXM. Polysaccharide that has been modified in this manner binds to polystyrene and polyvinyl chloride plates with a remarkable tenacity.

Assay of patient sera

Sera are obtained and is placed into two categories: (1) HIV-infected patients who did or (2) did not develop cryptococcosis once the HIV infection progressed to AIDS. IgG antibodies are measured at a significantly higher frequency in the patient group who developed cryptococcosis than in the patient group who did not develop cryptococcosis.

The present invention provides new information regarding anti-GXM antibodies which occur in serum obtained from normal adult donors. The frequency of occurrence of anticryptococcal IgM antibody in sera was about 98% of normal donors, whereas IgG antibody occurred at a frequency of 28% of normal donors. The present invention illustrates a striking reduction in the occurrence of anti-GXM antibodies of the IgM class in all categories of HIV-positive patients. A similar reduction was seen in the occurrence of antibodies with kappa light chains. In contrast, there was no reduction in the percentage of HIV-positive patients producing antibodies with lambda light chains. A significant reduction in the occurrence of IgG antibodies was not found in patients at various stages of HIV infection. This indicates that the IgG antibody marker for risk for cryptococcosis is not lost as the immune system deteriorates in the progression to AIDS.

Decreased responses to Type 2 T-independent antigens have been previously found to occur relatively early in the course of HIV infection. Previous studies of the immune response to pneumococcal vaccines found impaired IgG2, IgM and IgA responses in HIV positive patients with persistent generalized lymphadenopathy; there was no loss of the IgG1 response. Thus, the decrease in anti-GXM IgG antibodies may be due to a selective loss of IgG2. This would be consistent with the occurrence of IgG1 in two of five normal sera that were examined.

The antigenic stimulus for the anti-GXM antibodies in normal human serum is unknown. The antibodies could be due to stimulation by cross-reactive antigens that are encountered in the environment. "Natural" antibodies reactive with several bacterial capsules are believed to be due to exposure to cross-reacting antigens of nonpathogenic enteric and nasopharyngeal organisms. Glucuronic acid and O-acetyl groups are common components of many polysaccharides. Thus, it is possible that the ubiquitous anti-GXM IgM antibody is reactive with one of these components. On the other hand, xylose is not characteristically found in bacterial capsules, although it is common among plants. The IgG anti-GXM antibody may represent exposure to cryptococci either in nature or as a subclinical infection. Thus, anti-GXM IgG would be a marker for latent cryptococcal infection and increased risk for cryptococcosis in HIV infected or other immunocompromised patients.

All patents and publications mentioned in this specification are indicative of the levels of those skilled in the art to which the invention pertains. Any patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of identifying immunocompromised individuals who are at high risk for development of cryptococcosis, comprising the step of measuring the titer of IgG antibody to glucuronoxylomannan in sera of said individuals, wherein a positive result obtained with a dilution of more than 1/10 is a positive titer, and wherein said positive titer identifies an individual at high risk for development of cryptococcosis.

2. The method of claim 1, wherein said immunocompromised individuals are in a pathophysiological state selected from the group consisting of the Acquired Immune Deficiency Syndrome, supraphysiologic doses of adrenal corticosteroids, sarcoidosis and lymphoma.

3. The method of claim 1, wherein said individuals are infected with the Human Immunodeficiency Virus.

4. The method of claim 1, wherein said antibody is measured by an enzyme linked immunosorbent assay.

5. The method of claim 4, wherein glucuronoxylomannan is immobilized on microtiter plates.

6. The method of claim 5, wherein immobilization requires chemical modification of glucuronoxylomannan in a manner which preserves antigenic structure while increasing hydrophobicity.

7. The method of claim 6, wherein tyramine is bound to glucuronoxylomannan via benzoquinone coupling, and wherein pH of the reaction does not exceed about 8.5.

* * * * *

UNITED STATES PATENT AND TRADEMARK OFFICE
CERTIFICATE OF CORRECTION

PATENT NO. : 5,677,137
DATED : October 14, 1997
INVENTOR(S) : Kozel

It is certified that error appears in the above-identified patent and that said Letters Patent is hereby corrected as shown below:

In Column 1, line 34, "pneumocystis" should read --pneumocystitis--.

In Column 1, line 42, please insert the word --of-- between the words "used" and "treat".

In Column 2, line 3, please remove the colon between the words "of" and incubating".

In Column 2, line 27, please remove the colon between the words "of" and "measuring".

In Column 2, line 56, please insert a comma after "(squares)".

In Column 2, line 65, "4°" should read --4°C.--.

Signed and Sealed this

Thirteenth Day of February, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

Page 2 of 2

PATENT NO. : 5,677,137
DATED : October 14, 1997
INVENTOR(S) : Kozel

It is certified that error appears in the above-identified patent and that said Letters Patent is hereby corrected as shown below:

In Column 2, line 66, please insert a comma after "(squares)".

In Column 2, line 67, "tyramylated" should read --tyraminated--.

In Column 3, line 6, please remove the comma after "(circles)" and replace with a semi-colon.